US00PP07833P

United States Patent [19]

DeLeon

[11] Patent Number: Plant 7,833

[45] Date of Patent: Mar. 17, 1992

[54] AECHMEA HYBRID 'EILEEN'

[75] Inventor: Nat DeLeon, Miami, Fla.

[73] Assignee: DeLeon's Bromeliad World, Inc., Goulds, Fla.

[21] Appl. No.: 544,112

[22] Filed: Jun. 22, 1990

[51] Int. Cl.[5] ..... A01H 5/00

[52] U.S. Cl. ..... Plt./88

[58] Field of Search ..... Plt./88, 88.8

*Primary Examiner*—Howard J. Locker

*Attorney, Agent, or Firm*—Cushman, Darby & Cushman

[57] ABSTRACT

A new and distinct Aechmea hybrid cultiver obtained by crossing (*Aechmea Fasciata*×*Aechmea serrata*) with *Aechmea serrata*, substantially as herein shown and described, characterized as to novelty by the unique combination of the spineless habit of the leaves, and a large, upright, heavily-branched inflorescence bright rose in color, which stays in color for several months.

3 Drawing Sheets

BACKGROUND OF THE INVENTION

My present invention is that of a new and distinct hybrid in the genus Aechmea which is the result of crossing a hybrid of my own origination with one of its parent species.

Over the past 25 years, I have been actively engaged in hybridizing bromeliads, using most bromeliad genera, and have produced numerous hybrids. One genus I have been most interested in for the past 10 years is the genus Aechmea. Hybridizing among the Aechmea presents a challenge. Unlike other genera, such as Vriesea and Neoregelia, most Aechmea hybrids prove sterile. Occasionally, one finds an Aechmea hybrid that is not sterile, but the only way one can determine whether a hybrid is fertile is to attempt pollination.

Approximately 10 years ago, I created a hybrid by crossing *Aechmea serrata* with *Aechmea fasciata*. This cross resulted in a plant of no special note. It grew well, but the foliage lacked any striking character and the inflorescence was small in relation to the size of the plant. Four years ago, in the course of my hybridization activities, I decided to back cross this hybrid with bot of its parent species, using the parent species as the pollen contributors. The pollinating of (*Aechmea serrata*×*Aechmea fasciata*) by *Aechmea fasciata* produced nothing. The cross was apparently sterile. However, the pollinating of (*Aechmea serrata*×*Aechmea fasciata*) by *Aechmea serrata* was successful. Pollinated some 30 times, a few seeds were produced. Of a total of 17 seeds sowed, only 9 germinated.

SUMMAYR OF THE INVENTION

As can be expected in crossing a hybrid with a species, the offspring differed from one another. Remarkably, among these seedlings I discovered two which were spineless. The species *Aechmea fasciata* and *Aechmea serrata* both possess leaves edged with sharp spines, as does the hybrid *A. fasciata*×*A. serrata*. Of the 9 plants grown from my new cross, one plant stood out from the rest and fortunately it was one of the spineless seedlings. Its branched inflorescence was larger than any of the others, and bore more branches. The inflorescence is a deep, bright rose in color and is particularly long-lasting, staying in good color for over five months. As it blooms the inflorescence continues to elongate to up to 15 inches in length. It resembles nothing that I have ever seen, grown or read about in more than 30 years of growing bromeliads. As a result, there in no variety to which I can compare it in order to highlight its distinguishing characters. I have named this new cultivar Aechmea 'Eileen'.

The plant was grown in cultivated places, initially at Miami, Fla, and more recently at Goulds, Fla. I have successfully reproduced it asexually by division of basal suckers at Goulds, Fla., with the characters of the plant remaining true. It has not yet been determined that tissue culture propagation can be successfully employed.

BRIEF DESCRIPTION OF THE DRAWINGS

The accompanying photographs clearly depict the spineless character of the leaves and the inflorescence of the new invention.

Sheet 1 shows the overall character of a typical plant of the new cultivar Aechmea 'Eileen'.

Sheet 2: shows a close up of the underside of the leaves illustrating leaf scaling and the spineless character of Aechmea 'Eileen'.

Sheet 3: shows the upper leaf surface of Aechmea 'Eileen' which again illustrates its spineless character.

DETAILED DESCRIPTION

A botanical description has been prepared by Harry Luther, Director of the Bromeliad Identification Center located at the Marie Selby Botanical Gardens in Sarasota, Fla. His description was based on a living plant and was done by visiting the nursery in Goulds, Fla, where the plant has been grown. The botanical description is as follows:

Plant: Flowering to 75 cm tall.

Leaves: Rosulate, spreading, ca. 18 in number, to 70 cm long, appressed lepidote adaxially, conspicuously pale pruinose lepidote abaxially, dark green.

Leaf:

*Sheaths.*—Broadly elliptic, to 20 cm long, 14 cm wide, more or less concolorous with the blades, entire.

*Blades.*—Ligulate, subacute to rounded, apiculate, to 10 cm wide, entire.

Scape: Erect, exceeding the leaf sheaths, stout, 30 cm long, 18 mm thick, rose, densely white lepidote.

*Bracts.*—erect, imbricate, lanceolate, to 13 cm long, bright rose, pale lepidote, entire.

In florescence: Densely tripinnate, to 38 cm long, 26 cm broad, pale lepidote except for the petals.

Primary bracts: Like the scape bracts but mostly reflexed, decreasing evenly in size toward the apex of the inflorescence, rose, entire.

Spikes: Stipitate, erect to spreading, polystichously-flowered, 6–20 cm long.

Floral bracts: Broadly elliptic, mucronate, 12–16 mm long, thin, nerved, purple rose.

Flowers: Sessile, erect to slightly spreading.

Sepals: Asymmetrical, 13–15 mm long, mucronate, purple rose.

Corolla: Erect, only slightly spreading.

Petals: Ligulate, obtuse, to 25 mm long, each appendaged with two basal scales, blue lavendar with a paler apex.

Ovary: Ellipsoid 8–10 mm long, pale pink or cream.

Coloration

As an aid to understanding the coloration of my new variety, its coloration has been observed and compared with color plates from a standard reference work, namely the Munsell Limit Color Cascade (M.L.C.C.) published by Munsell Color Company. The observations were made under natural daylight in the nursery where the plants are grown, from plants grown under standard polypropylene shadecloth giving 73% shade, which plants had received once per week fertilizing with a liquid fertilizer (20-20-20) injected into the irrigation sprinkler system used for watering them. (The green leaf coloration can vary according to light exposure and fertilization. Light exposure brighter than 65% shade has a bleaching effect on leaf color, particularly during the summer months. If fertilizer levels are not maintained, leaf color will be lighter. Exposure to full sun for an hour or more will burn all plant parts.)

Leaves: Both of the upper and lower leaf surfaces are dark green (M.L.C.C. No. 17-14). The surface of the underside of the leaves if often completely covered with silver-white trichomes. The upper leaf surface is only sparsely covered with silver-white trichomes.

Floral and scape bracts: Rosy-pink (M.L.C.C. No. 38-5) at anthesis, changing to a deep rose (M.L.C.C. No. 38-7) after all flowers have become spent. The colors are somewhat masked by the presence of silver-white trichomes. The presence of trichomes can make the floral bracts appear lighter in color than the scape bracts.

Sepals: The sepals are very evident since they are not fully covered by the floral bracts. The basal portion of the sepal (bearing the three ovary cells) is a creamy white that does not change color with age. The upper portion of the sepal, nearly two-thirds of its length, is a lighter pink (M.L.C.C. No. 37-3), deepening in color after all flowers are spent to a purplish pink hue (M.L.C.C. No. 44-7). The sepals are dusted with silver-white trichomes that become more prominent with age.

Flowers: The insignificant flowers, each lasting only one day, have blue petals (M.L.C.C. No. 3-7) which do not open. After one day, the petals turn black.

Additional Distinguishing Characteristics

The flowers of my new variety bear no pollen, and several attempts at cross-pollination with the pollen of other varieties have always met with failure. Therefore, I consider the plant to be sterile.

Plants of the new variety have shown no peculiar susceptibility to fungus or insect pests, but do exhibit hybrid vigor in growth.

The inflorescence remains in good color for up to six months. Flowering is easily induced artifically by treatment with Florel bloom inducer, at the rate of one teaspoon per gallon of water. The inflorescence will show commercially acceptable color in eleven or twelve weeks after treatment during the warm summer months, and in twelve to fourteen weeks after treatment during the cooler winter months, in the conditions existing in Sourthern Florida. This is a commercially important factor since many commercially grown bromeliad genera, such as Guzmania, Vriesea and Tillandsia, can require twice as long, or longer, to produce commercially acceptable inflorescences following hormone treatment to induce flowering. Once flowering is initiated, the plants can go several weeks without watering due to the water held in the tank formed by the leaves, thereby enhancing the retail shelf-life of the plant.

I claim:

1. A new and distinct Aechmea hybrid cultivar obtained by crossing (*Aechmea fasciata* × *Aechmea serrate*) with *Aechmea serrata*, substantially as herein shown and described, characterized as to novelty by the unique combination of the spineless habit of the leaves, and a large, upright, heavily-branched inflorescence bright rose in color, which stays in color for several months.

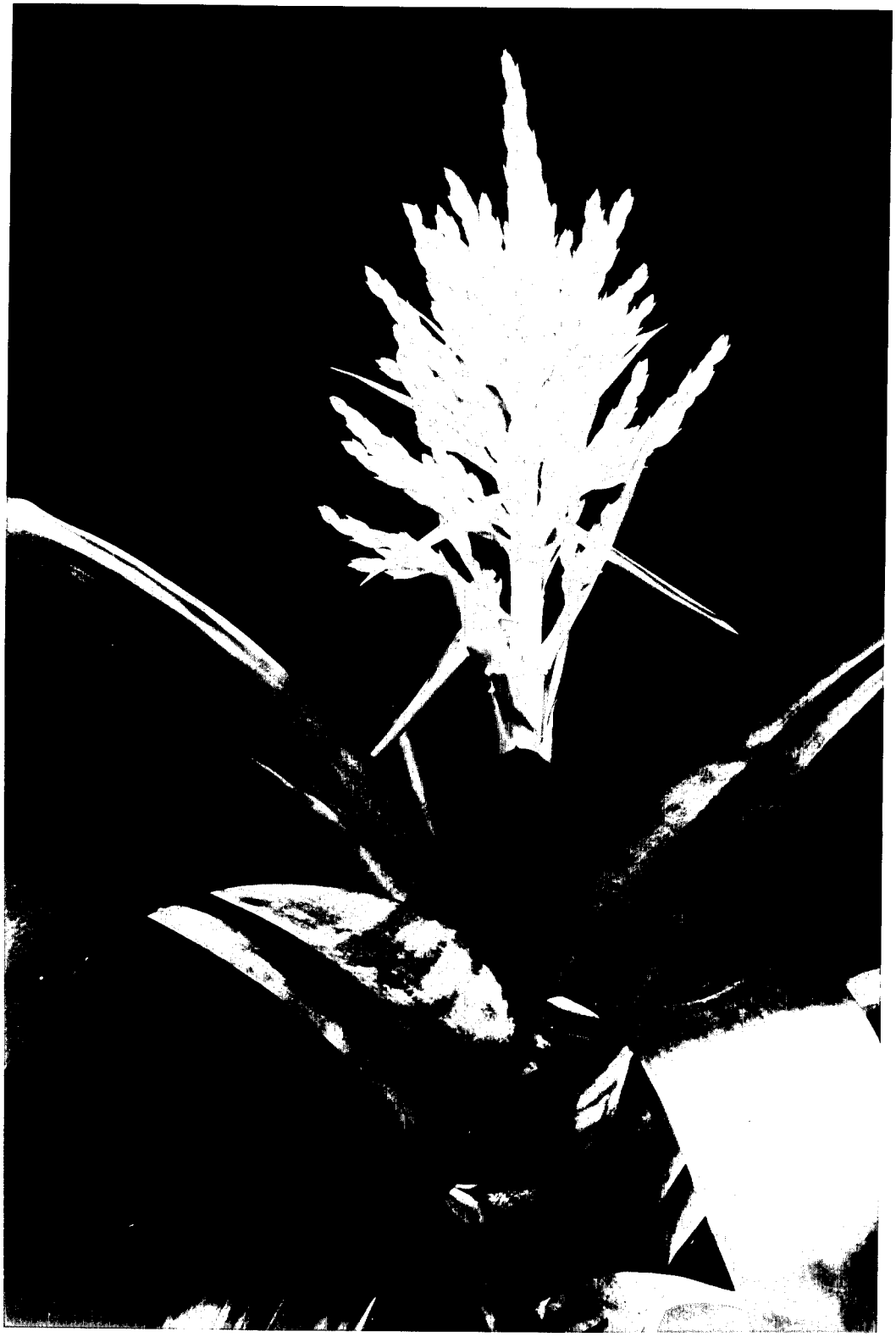

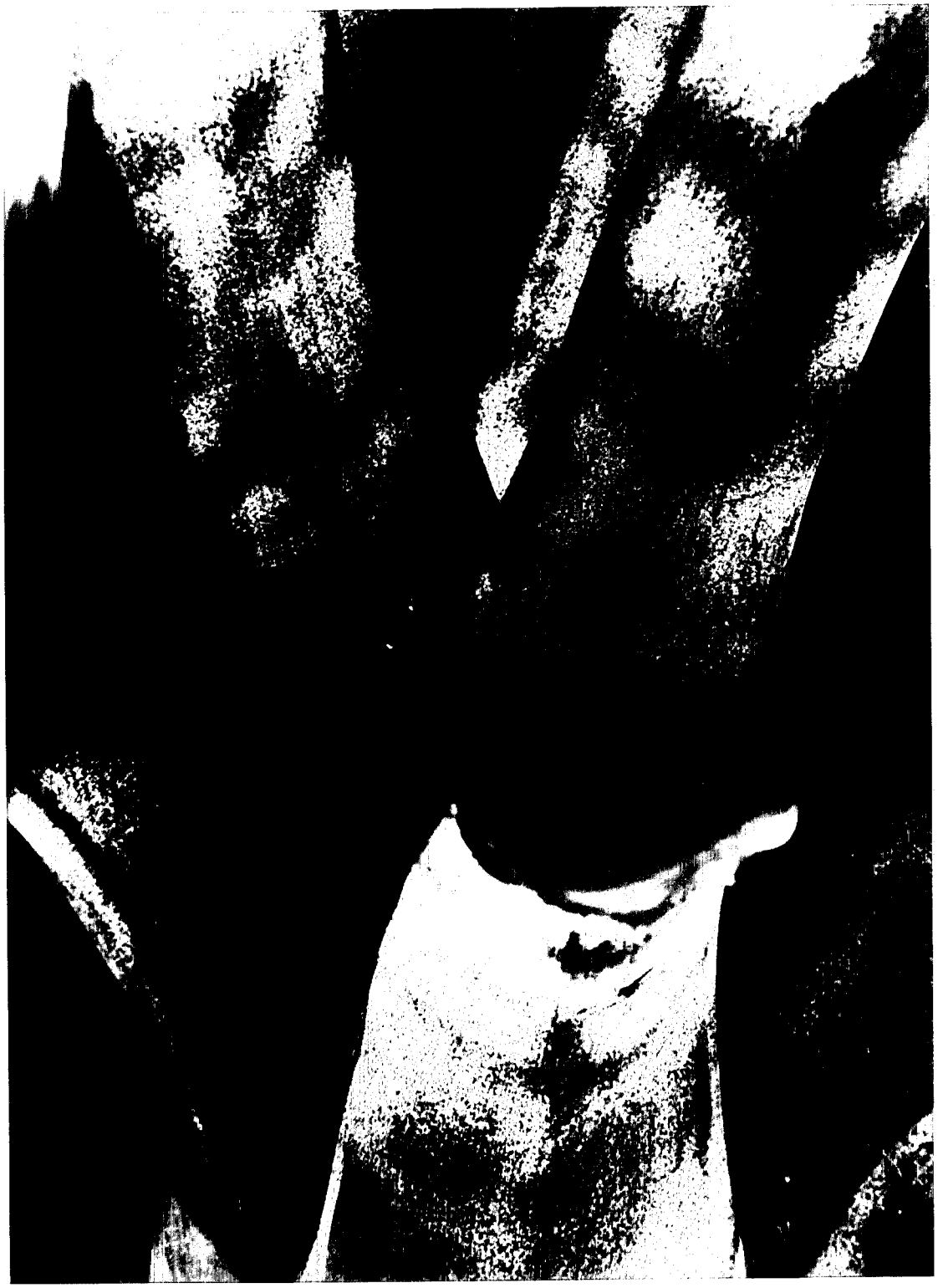

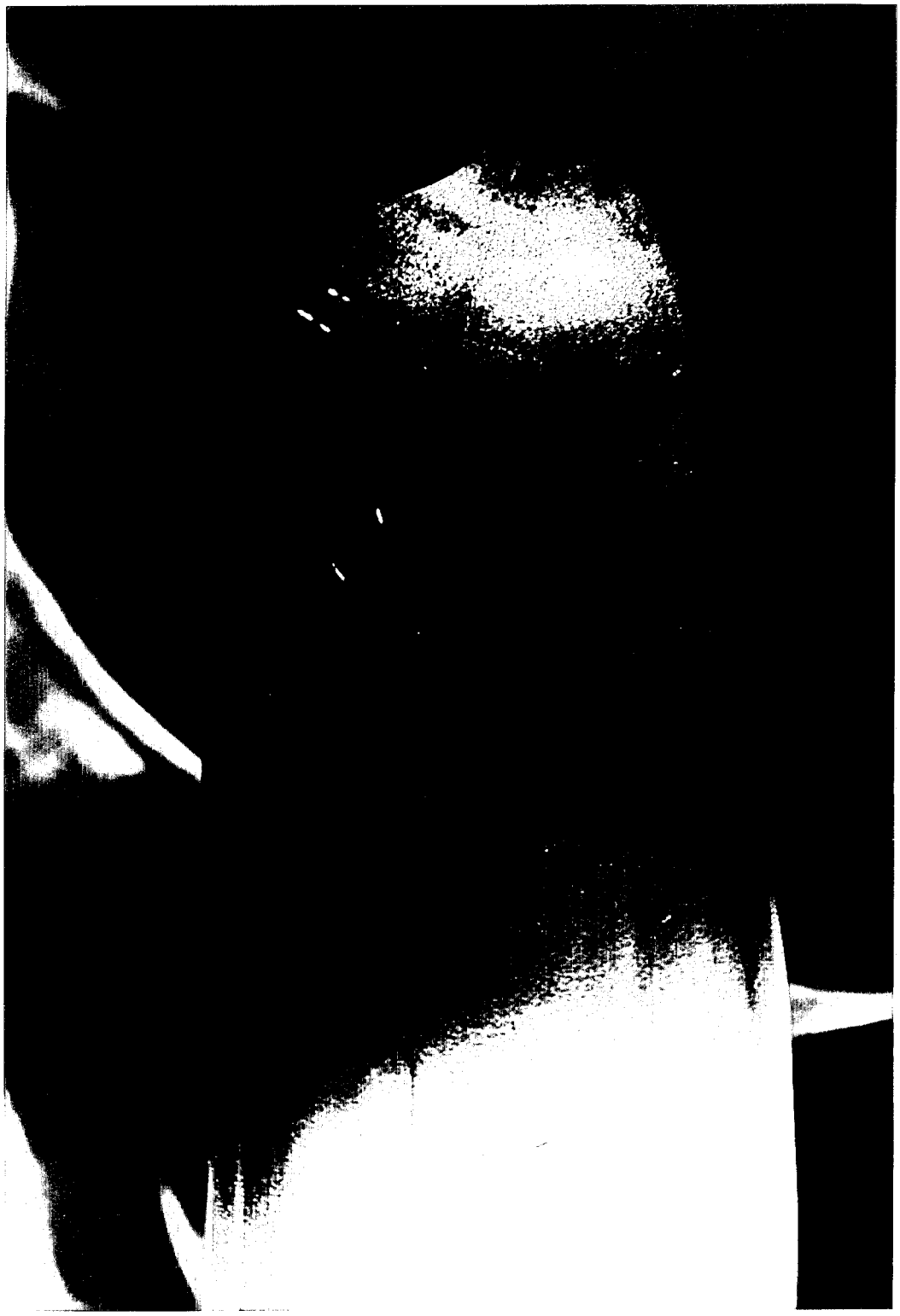

* * * * *